United States Patent
Poland et al.

(10) Patent No.: US 11,696,745 B2
(45) Date of Patent: Jul. 11, 2023

(54) OPTIMAL SCAN PLANE SELECTION FOR ORGAN VIEWING

(71) Applicant: KONINKLIJKE PHILIPS N.V., Eindhoven (NL)

(72) Inventors: McKee Dunn Poland, Andover, MA (US); Balasundar Iyyavu Raju, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 90 days.

(21) Appl. No.: 16/492,181

(22) PCT Filed: Feb. 27, 2018

(86) PCT No.: PCT/EP2018/054838
§ 371 (c)(1),
(2) Date: Sep. 9, 2019

(87) PCT Pub. No.: WO2018/166789
PCT Pub. Date: Sep. 20, 2018

(65) Prior Publication Data
US 2021/0137498 A1 May 13, 2021

Related U.S. Application Data

(60) Provisional application No. 62/472,031, filed on Mar. 16, 2017.

(51) Int. Cl.
*A61B 8/00* (2006.01)
*A61B 8/08* (2006.01)

(52) U.S. Cl.
CPC .......... *A61B 8/483* (2013.01); *A61B 8/0883* (2013.01); *A61B 8/0891* (2013.01);
(Continued)

(58) Field of Classification Search
CPC ..... A61B 8/483; A61B 8/4444; A61B 8/0883; A61B 8/54; A61B 8/463; A61B 8/0891
See application file for complete search history.

(56) References Cited

U.S. PATENT DOCUMENTS

| 6,013,032 A | 1/2000 | Savord |
| 6,443,896 B1 | 9/2002 | Detmer |

(Continued)

FOREIGN PATENT DOCUMENTS

| EP | 2345908 A2 * | 7/2011 | .......... G01S 7/5205 |
| EP | 2345908 A2 | 7/2011 | |

(Continued)

OTHER PUBLICATIONS

PCT International Search Report, International application No. PCT/EP2018/054838, dated Jul. 2, 2018.

(Continued)

*Primary Examiner* — Christopher Koharski
*Assistant Examiner* — Taylor Deutsch

(57) ABSTRACT

The present disclosure describes an ultrasound imaging system configured to identify a scan line pattern for imaging an object or feature thereof. The system may include a controller that controls a probe for imaging a volume of a subject by transmitting and receiving ultrasound signals in accordance with a plurality of scan line patterns. One or more processors communicating with the probe may generate a plurality of image data sets based on the signals received at the probe, each data set corresponding to a discrete scan line pattern. These data sets are assessed for a target characteristic specific to the object targeted for imaging. One the data set that includes the target characteristic is identified, the one or more processors select the scan line pattern that corresponds the identified image data set. This (Continued)

scan line pattern may then be used for subsequent imaging of the volume to view the object.

22 Claims, 6 Drawing Sheets

(52) U.S. Cl.
CPC ............ *A61B 8/4444* (2013.01); *A61B 8/463* (2013.01); *A61B 8/54* (2013.01)

(56) References Cited

U.S. PATENT DOCUMENTS

| | | | |
|---|---|---|---|
| 2006/0058651 A1 | 3/2006 | Chiao | |
| 2010/0312112 A1* | 12/2010 | Kamiyama | ............... G06T 7/12 600/443 |
| 2012/0150036 A1 | 6/2012 | Buckton | |
| 2015/0002538 A1* | 1/2015 | Sohn | .................... G06T 7/0012 345/629 |
| 2015/0011886 A1* | 1/2015 | Radulescu | ............ A61B 8/585 600/447 |
| 2015/0150447 A1* | 6/2015 | Huang | ................... A61B 3/102 382/131 |
| 2017/0323447 A1* | 11/2017 | Tsukagoshi | ............ A61B 6/545 |
| 2018/0153505 A1* | 6/2018 | Cadieu | ................. A61B 8/4254 |
| 2018/0263593 A1* | 9/2018 | Dickie | ................. A61B 8/0841 |

FOREIGN PATENT DOCUMENTS

| | | |
|---|---|---|
| JP | H04224738 A | 8/1992 |
| KR | 20160117110 A | 10/2016 |
| WO | 2009044316 A1 | 4/2009 |
| WO | WO2018108742 A1 | 6/2018 |

OTHER PUBLICATIONS

Letter and Amendment in Response to the International Search Report and the Written Opinion of the International Searching Authority Under Article 34, Dorsey & Whitney, dated Nov. 30, 2018.

Moshavegh Ramin et al., "Novel Automatic Detection of Pleura and B-Lines (Comet-Tail Artifacts) on In Vivo Lung Ultrasound Scans", Progress in Biomedical Optics and Imaging, SPIE—International Society for Optical Engineering, Bellingham, WA, US, vol. 9790, Apr. 1, 2016 (Apr. 1, 2016), pp. 9790OK-9790OK, XP060065636.

* cited by examiner

OPTIMAL SCAN PLANE SELECTION FOR ORGAN VIEWING

CROSS REFERENCE TO RELATED APPLICATIONS

This patent application claims the priority benefit under 35 U.S.C. § 371 of International Patent Application no. PCT/EP2018/054838, filed Feb. 27, 2018, which claims the benefit of and priority to U.S. Provisional Application No. 62/472,031, filed Mar. 16, 2017, which is incorporated by reference herein in its entirety.

BACKGROUND

Ultrasound imaging has traditionally been performed by users with specialized training in ultrasound techniques, such as sonographers and radiologists. Ultrasound imaging is being increasingly used by non-traditional personnel outside of well-trained sonographers and radiologists. To view internal patient features, diagnose various conditions, and even provide ultrasound therapy, it is critical that such users, despite their lack of experience, are able to obtain accurate and complete image data. Identifying a clinically significant image plane is a non-trivial task and typically requires skillful manipulation of an ultrasound probe. For example, in the context of lung imaging, certain imaging planes may be particularly useful for example in evaluating or identifying conditions such as lung sliding, extravascular lung water evaluation, consolidations, and others. If a proper imaging plane is not chosen, then the image data may not provide the necessary information for an accurate diagnosis. Accordingly, techniques for improving or simplifying the process of target image plane identification may be desired.

SUMMARY

Provided herein are ultrasound systems and methods for automated ultrasound imaging of various objects along a selected scan line pattern. Various examples transmit ultrasound signals in accordance with a plurality of scan line patterns into a subject after receiving an indication of an object, e.g., the heart or the lungs, to be imaged. The indication may be provided by a user selecting an option on a user interface. From the plurality of scan line patterns, a scan line pattern is identified and selected based on its inclusion of a target characteristic associated with the object to be imaged or a feature of the object. For subsequent imaging of the object along the selected scan line pattern, examples may involve automatically steering ultrasound beams in accordance with the selected scan line pattern. The systems disclosed herein may include a probe configured to transmit ultrasonic energy in different scan line patterns at the direction of a controller. One or more processors coupled with the probe may be configured to generate image data sets from the echo beams received at the probe, assess the image data sets for the target characteristic specific to the object targeted for imaging, identify the scan line pattern that includes the target characteristic, and select the scan line pattern for continued imaging. Further examples described herein involve additional processing steps taken to identify specific features and measure various parameters associated with such features.

In accordance with some examples, an ultrasound imaging system may include a controller. The controller may be configured to control a probe for imaging a volume of a subject, where imaging involves transmitting and receiving ultrasound signals in accordance with a plurality of scan line patterns. The system may further include one or more processors in communication with the probe. In some examples, the one or more processors may be configured to: generate a plurality of image data sets from the received ultrasound signals, each image data set corresponding to one of the scan line patterns; assess the image data sets for a target characteristic specific to an object in the volume; identify an image data set that includes the target characteristic; and select the scan line pattern, which corresponds to the identified image data set, for subsequent imaging of the volume.

In some examples, the target characteristic may be a characteristic of the object that meets an image quality threshold. In embodiments, the target characteristic may be an intensity level of a feature specific to the object. According to some of such examples, the object may be a lung and the feature may be a pleural line. In some implementations, the target characteristic may be the presence of a feature specific to the object. The object may be a lung and the feature may be a plurality of A-lines at multiple distances of a depth of a pleural line. In examples, the target characteristic may include a length or an area of a feature specific to the object.

In some embodiments, the scan line patterns may correspond to image planes. In some examples, the controller may be further configured to control the probe for imaging the volume of the subject by re-transmitting and receiving ultrasound signals in accordance with the plurality of scan line patterns upon detection of movement of the probe. In some examples, the probe may be a matrix probe and transmitting may involve electronically steering the ultrasound signals. In some examples, the probe may be a 1D array probe and transmitting may involve mechanically sweeping the ultrasound signals. Some embodiments may further include a display screen configured to display an image of the object obtained via the scan line pattern, which corresponds to the identified image data set, without displaying images obtained via other ones of the plurality of scan line patterns. The controller may be configured to automatically control the probe to obtain images, in real time, in accordance with the selected scan line pattern, and the system may further include a display screen configured to display the real-time images. The object may include a kidney, a heart, a blood vessel, or an internal cavity.

In accordance with some examples, a method may involve controlling a probe for imaging a volume of a subject, where imaging involves transmitting and receiving ultrasound signals in accordance with a plurality of scan line patterns; generating a plurality of image data sets from the received ultrasound signals, each image data set corresponding to one of the scan line patterns; assessing the image data sets for a target characteristic specific to an object in the volume; identifying an image data set that includes the target characteristic; and selecting the scan line pattern, which corresponds to the identified image data set, for subsequent imaging of the volume.

In some examples, the target characteristic may be a characteristic of the object that meets an image quality threshold. In some implementations, the target characteristic may be an intensity level of a feature specific to the object and/or the presence of a feature specific to the object. The object may include a lung and the feature may include a plurality of A-lines at multiple distances of a depth of a pleural line.

Additionally, any of the techniques for generating an ultrasound image of an object in the selected scan line pattern may be embodied in executable instructions stored on non-transitory computer-readable medium, which when executed cause a processor of a medical imaging system to be programmed to perform the processes embodied in the non-transitory computer-readable medium.

DETAILED DESCRIPTION

Figure 1:
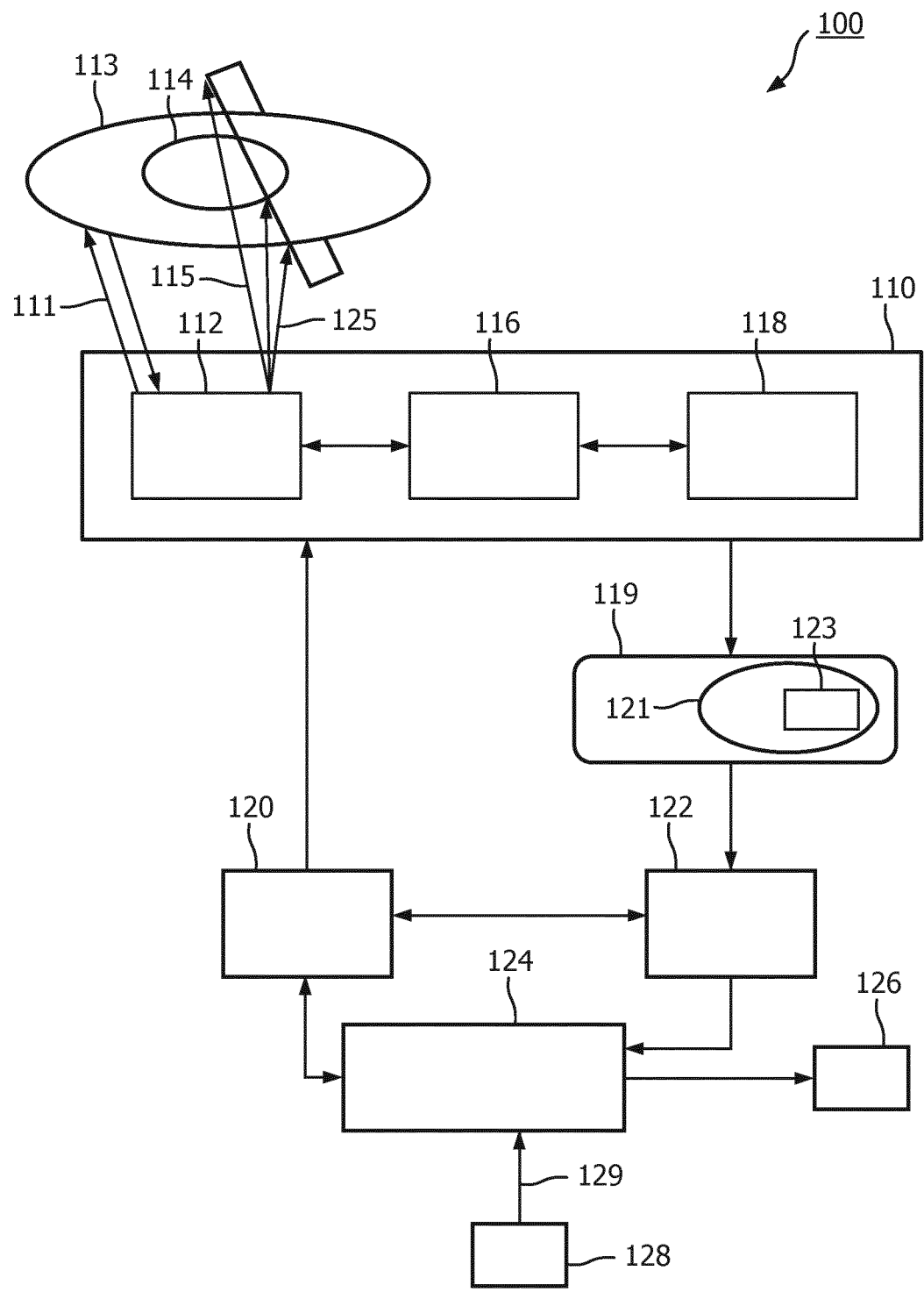
FIG. 1 is a block diagram of an ultrasound imaging system in accordance with the principles of the present disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The present technology is also described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer executable instructions. These computer executable instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

The quality of information, as well as the amount, collected via ultrasound imaging may vary drastically based on the experience level of the person operating the ultrasound equipment. Inadequate imaging of an internal feature of a subject may impede accurate medical evaluation of that feature and may prevent automated analysis programs from performing follow-on assessments. Sub-optimal positions and orientations of the ultrasound probe often cause the production of sub-optimal ultrasound images. Two-dimensional image planes used to visualize different slices of a subject within a 3D volume may be adjusted by varying transducer element delays, e.g., phased array beamforming, thereby providing different views of an internal feature, which may vary in quality. However, a user operating the ultrasound system may still be required to interpret the images obtained along each plane.

As provided herein, automated analysis of the images obtained along a plurality of scan line patterns may eliminate, or at least reduce, the likelihood of human error interfering with the imaging of various internal objects of a subject. In greater particularity, various internal objects, e.g., organs or structures within organs, may be associated with one or more features that appear during ultrasound imaging. Such features, when they appear, may be indicative of a clear image of the object being targeted. For example, horizontally-oriented ultrasound artifacts, known as "A-lines," may appear on an ultrasound image when scanning a lung. The A-lines may indicate that an optimized or enhanced image of the lung pleural interface has been obtained by the current position of the ultrasound probe. By detecting such features and in some cases, measuring one or more parameters of the features once detected, an imaging system may be configured to reliably and automatically identify a scan line pattern from which the best, or at least a clear, image of the object can be obtained, which may be referred to herein as the "target scan line pattern." Provided herein are automated systems and methods for visualizing various internal objects of a subject along a target scan line pattern without manual intervention.

FIG. 1 shows an example ultrasound system 100 configured to identify and select a target scan line pattern for imaging various patient objects in accordance with the present disclosure. As shown, the system 100 may include an ultrasound data acquisition unit 110. The ultrasound data acquisition unit 110 may include, in some embodiments, an ultrasound probe which includes an ultrasound sensor array 112 configured to transmit ultrasound signals or beams 111 into a 3D volume 113 containing an object 114 to be imaged, and receive signals 115 responsive to the transmitted beams. The data acquisition unit 110 may also include a beamformer 116 and a signal processor 118, which may be configured to generate a plurality of image data sets 119 from the received signals 115. The system 100 may also include a scan line controller 120 communicatively coupled with the ultrasound data acquisition unit 110 and configured to control the direction (i.e. steer) the transmit and receive beams. The system 100 may also include one or more processors, such as data processor 122, configured to select a target scan line pattern 125 based on the plurality of image data sets 119 received from the signal processor 118. The image data sets 119 may include data representative of a feature 121 and at least one target characteristic 123. In embodiments, the target characteristic 123 may include a characteristic of the object 114 that meets an image quality threshold, e.g., an intensity level of a feature specific to the object. In embodiments, the feature 121 may be a hypoechoic feature or a hyperechoic feature. The system 100 may also include a user interface 124 configured to receive user input 128, including an indication 129 of the object 114, and display ultrasound images 126, e.g., B-mode images, such as on a display screen operatively associated with the system 100. The configuration of the system 100 shown in FIG. 1 may vary. For instance, the system 100 can be stationary or portable. Various portable devices, e.g., laptops, tablets, smart phones, or the like, may be used to implement one or more functions of the system 100. In examples that incorporate such devices, the ultrasound sensor array 112 may be connectable via a USB interface, for example.

The ultrasound data acquisition unit 110 may be configured to acquire ultrasound data for one or more regions of interest selectable by a user, e.g., a sonographer, clinician or ultrasound technician. In conjunction with the beamformer 116, the ultrasound sensor array 112, in particular, may be configured to transmit ultrasonic signals in the form of ultrasound beams into a subject and receive ultrasound echoes responsive to the transmitted beams. The ultrasound sensor array 112 includes at least one transducer array configured to transmit and receive ultrasonic energy. According to embodiments of the present disclosure, a variety of transducer arrays may be used, e.g., linear arrays, convex arrays, or phased arrays. The number and arrangement of transducer elements included in the sensor array 112 may vary in different examples. For example, the ultrasound sensor array 112 may include a 1D or 2D array of transducer elements, corresponding to linear array and matrix array probes, respectively. The 2D matrix arrays may be configured to scan electronically in both the elevational and azimuth dimensions (via phased array beamforming) for 2D or 3D imaging. In some examples, a 2D matrix array may be configured to perform sub-array beamforming using a microbeamformer, for example as described in U.S. Pat. No. 6,013,032 (Savord), which is incorporated by reference in its entirety herein. One-dimensional arrays may be configured to scan 2D images electronically (via phased array beamforming) or additionally be mechanically swept across a region of interest in an orthogonal direction to the electrically scanned dimension in order to create 3D images.

In operation, the probe containing the ultrasound sensor array 112 may be held or secured in a stationary position while scanning is performed. Some embodiments may include an additional apparatus, e.g., an elongate arm, configured to hold the probe with the sensor array 112 in one position. According to such embodiments, a user may adjust the apparatus, either manually or by inputting instructions into an operating computer coupled with the apparatus, so that the apparatus positions the ultrasound sensor array 112 over the region of interest, e.g., over a chest region. In other embodiments, the user may simply hold the probe with the ultrasound sensor array 112 manually in one position on the surface of the subject while scanning is performed. In still other embodiments, the probe with the ultrasound sensor array 112 may include an adhesive or one or more straps configured to secure the probe to the surface of the subject being imaged.

The data acquisition unit 110 may also include a beamformer 116, e.g., comprising a microbeamformer or a combination of a microbeamformer and a main beamformer, coupled to the ultrasound sensor array 112. The beamformer 116 may control the transmission of ultrasonic energy, for example by forming ultrasonic pulses into focused beams. The beamformer 116 may also be configured to control the reception of ultrasound signals such that discernable image data may be produced and processed with the aid of other system components. The role of the beamformer 116 may vary in different ultrasound probe varieties. In some embodiments, the beamformer 116 may comprise two separate beamformers: a transmit beamformer configured to receive and process pulsed sequences of ultrasonic energy for transmission into a subject, and a separate receive beamformer configured to amplify, delay, and/or sum received ultrasound echo signals. In some embodiments, the beamformer 116 may comprise a microbeamformer operating on groups of sensor elements for both transmit and receive beamforming, coupled to a main beamformer which operates on the group inputs and outputs for both transmit and receive beamforming, respectively.

The operation of the data acquisition unit 110 may be controlled by the scan line controller 120, which may be physically, operatively, and/or communicatively coupled to the data acquisition unit. The scan line controller 120 may include one or more processors, e.g., a computational module or circuitry, configured to receive an indication 129 of a desired object 114 to be imaged, and based on this indication, manipulate the data acquisition unit 110 to scan a 3D volume. An object 114 may include one or more bodily structures or tissues, including, for example, the heart and/or sub-components thereof, e.g., the left ventricle of the heart. A non-exhaustive list of other possible objects may include various organs, e.g., kidneys, bones, blood vessels, internal cavities, and/or interfaces, e.g., the pleural interface of the lung. By selecting an object 114, a user effectively instructs the scan line controller 120 to initiate the scanning necessary to identify a target scan line pattern 125 that increases, enhances, and/or maximizes the quality of the ultrasound image of the object. Each scan line pattern 125 may vary in shape and orientation. For instance, a scan line pattern 125 may include an image plane (illustrated by the dashed lines in FIG. 1), a frustum, a sector, a slab (multiple combined image planes), or a wedge of equally spaced scan lines.

Before its receipt at the scan line controller 120, the indication 129 of the object 114 to be imaged may be initially received at a user interface 124, which may be operatively, physically, and/or communicatively coupled with the ultrasound sensor array 112 via the controller 120. The user interface 124 may be configured to receive manual, electronic, and/or wireless input from a user. In some examples, the user interface 124 may be a touch screen. The user interface 124 may include a plurality of options or presets for user selection, each option representing at least one patient object that may be imaged. For example, one option may read "lung pleural interface," while another may read "left ventricle." Selecting an option displayed on the user interface 124 may prompt the ultrasound sensor array 112 of the data acquisition unit 110, at the direction of the transmit scan line controller 120, to automatically scan a 3D volume of a patient in search of the selected object 114. In some examples, the ultrasound sensor array 112 may not initiate the scan until a second option is selected at the user interface 124. Selectable second options may include "auto optimize" or "begin search," for example.

In response to receiving the indication 129 of the object 114 to be imaged from the user interface 124, the controller 120 may be configured to automatically control the ultrasound data acquisition unit 110, specifically the ultrasound sensor array 112, to transmit ultrasound beams 111 and receive signals 115 in accordance with a plurality of scan line patterns. In some examples, each scan line pattern may be configured to acquire data, e.g., image data, corresponding to a single image plane through the 3D volume 113. The 3D volume includes the object 114 selected by the user. For instance, if the object 114 selected is the heart, the 3D volume scanned by the ultrasound sensor array 112 at the direction of the controller 120 may be a chest region of the subject. Different scan line patterns may be successively stepped through the volume containing the object 114 during a scan such that collectively, a plurality of scan line patterns may scan the entire 3D volume.

In various embodiments, the manner by which the plurality of scan line patterns are generated and/or swept through the 3D volume may vary and may depend on the type of ultrasound sensor array 112 being utilized. For instance, embodiments utilizing a matrix probe may involve electronically steering ultrasound beams 111 through the volume by activating different groups of transducer elements at different times and by controlling the timing of transmit pulses and detected receive pulses in groups of transducer elements, i.e. by transmit and receive beamforming. In particular, a matrix probe may be configured to transmit a plurality of individual scan lines along an azimuthal scan plane that is successively stepped in the elevational direction until the entire 3D volume is scanned. In this manner, electronically steering the plurality of scan line patterns may create a series of rastered scan planes. In other examples, a matrix probe may be configured to rotate an azimuthal or elevational scan plane through a 3D volume by varying an angle of rotation about a center scan line. Additional modes of generating different scan line patterns using a matrix probe may also be implemented in accordance with the present disclosure.

Other embodiments may employ a 1D array probe configured to mechanically steer an array of transducer elements across a 3D volume. In specific embodiments, the 1D array may be swept in a pendulum-like fashion throughout an arc, such that the set of 2D scanned planes generated therefrom form the 3D volume. Such mechanical steering may be driven by a motor physically or operatively coupled with the ultrasound sensor array 112.

In some embodiments, the scan line controller 120 may be further configured to control the speed at which the ultrasound beams 111 are steered across the target volume 113. For example, in some situations a relatively fast sweep through the volume may be desired, while in others, a slower speed may be more appropriate. If the object to be imaged is constantly moving, e.g., the heart, the speed at which the ultrasound sensor array 112 switches between different scan line patterns may be reduced to capture image data of the object 114 at every configuration thereof. The reduction is typically achieved either by reducing the number of scan lines in the pattern (e.g., spreading them further apart in space), or by processing a plurality of parallel receive beams in the close vicinity of a given transmit beam. More particularly, the scan line controller 120 may direct the ultrasound sensor array 112 to transmit ultrasound beams 111 along individual scan line patterns 125 in about 0.5 to about 1.5 second intervals before switching to the next scan line pattern. This approach may ensure that each scan line pattern captures ultrasound data of the heart, for example along a given image plane, throughout the full expansion and contraction of cardiac tissue associated with every heartbeat. Similar adjustments may be implemented for imaging the lungs to account for changes in lung shape and cross-sectional area that occur when a subject inhales and exhales. The time intervals may vary for different features. In various embodiments, the scan speed may be defined and/or adjusted by a user or automatically selected by the scan line controller 120.

As further shown in FIG. 1, at least one processor, such as signal processor 118, may be communicatively, operatively, and/or physically coupled with the ultrasound sensor array 112. The signal processor 118 may be configured to generate a plurality of image data sets 119 from the signals 115 received at the ultrasound sensor array 112 responsive to the transmitted ultrasound beams 111. Each of the image data sets 119 may correspond to a single scan line pattern 125. Information embodied in the image data may relate to the appearance of various objects, including but not limited to the specific object 114 selected by the user for imaging. The data may also include information regarding the spatial location and/or brightness intensity of one or more features associated with the object 114. The image data collected by the signal processor 118 may be received and analyzed for particular information by the data processor 122 based on the object 114 selected.

The illustration shown in FIG. 1 depicts the data processor 122 coupled with the data acquisition unit 110. In embodiments, the data processor 122 may be operatively, physically, and/or communicatively coupled with one or all components of the data acquisition unit 110. In particular examples, the data processor 122 may be directly coupled to the signal processor 118, such that the image data sets 119 generated by the signal processor may be immediately received and processed by the data processor. Before analyzing the data received from the signal processor 118, the data processor 122 may be configured to select a feature 121 based on the object 114 selected by the user. In some examples, selection of the feature 121 may be performed immediately by the data processor 122 following receipt of the indication 129 of the feature at the controller 120, which as further shown in FIG. 1, may also be coupled with the data processor 122. The data processor 122 may be programmed to associate each object 114 with one or more features 121 and target characteristics 123.

In general terms, the feature 121 may be a characteristic indicative of the object 114 to be imaged, and thus may vary from object to object. The feature 121 may be a tangible, physical characteristic of the object 114, or a visual artifact of ultrasound imaging. For example, if the object 114 to be imaged is a lung, the feature 121 may include a pleural line and/or one or more A-lines. The pleural line, or pleural interface, is the physical boundary between the chest wall and the lung. Detection of the pleural line may indicate that a satisfactory image of the lung has been obtained. Detection of the pleural line may also be critical for monitoring specific conditions, e.g., lung sliding. A-lines, by contrast, are merely visual artifacts generated by reverberating ultrasound echoes that may be especially bright when ultrasound beams reflect off the pleural interface at a perpendicular angle. A-lines may appear at multiple distances of a depth of the pleural line. Identification of the pleural line and one or more A-lines may be performed by any of the processing techniques disclosed in related US Patent Application titled "Target Probe Placement for Lung Ultrasound" and naming Balasundar et al., which is incorporated by reference in its entirety herein. As another example, if the object 114 to be imaged is the kidney, the feature 121 may include one or more twinkling artifacts, which may each appear as a discrete focus of alternating colors during color Doppler imaging of rough reflective surfaces, for example.

Out of the plurality of scan line patterns 125 generated by the ultrasound data acquisition unit 110, the data processor 122 may be configured to assess the image data sets 119 for a target characteristic 123 specific to the object 114 and identify an image data set that includes the target characteristic 123. The target characteristic 123, and the means implemented to assess it, may vary in embodiments. In some embodiments, the target characteristic 123 may be the presence of a feature 121 specific to the object 114. For instance, in embodiments where the object 114 is a lung, the feature 121 may include a plurality of A-lines, and the target characteristic 123 may comprise the presence of the A-lines. According to such embodiments, the processor 122 may be configured to select for subsequent imaging the scan line pattern 125 that corresponds to the image data set 119 containing the A-lines. In various examples, the target characteristic 123 may include a length and/or cross-sectional area of a feature 121, which may be hypo- or hyperechoic. In some examples, the target characteristic 123 may comprise a characteristic of the object 114 or feature 121 thereof that satisfies an image quality threshold. The threshold may be a maximum, a minimum, or a pre-set value. For example, in mobile ultrasound applications, where processing power may be limited, the image quality threshold may be satisfied by a lower pre-set value than in stationary or at least less-portable systems, e.g., car-based systems which generally have more processing resources. In particular embodiments, the target characteristic 123 may be an intensity level of the feature 121 specific to the object 114. The intensity level may be a maximum or minimum intensity level determined by comparing measured intensity levels of the feature 121 acquired in multiple image data sets, or the intensity level may be a predefined value. Thus, the data processor 122 may be configured to assess the image data sets 119 for the target characteristic 123 by comparing multiple image data sets 119. In embodiments, image data sets may be iteratively compared, for example frame-by-frame as the scan line patterns 125 are adjusted, or at the end of a full scan. In the lung example introduced above, for instance, the data processor 122 may be configured to identify the scan line pattern 125 that maximizes the brightness of the pleural line and/or one or more A-lines. In another example, the object 114 to be imaged may be a blood vessel, e.g., an artery or a vein, and the data processor 122 may be configured to determine the scan line pattern 125 in which the cross-sectional area of that blood vessel is maximized. In another example, the data processor 122 may be configured to identify the scan line pattern 125 in which the hypoechoic area of the left ventricle of the heart is maximized. In another example, the data processor 122 may be configured to identify the scan line pattern that contains the maximal length of one or more heart valves, such as the mitral valve. In still another example, the data processor 122 may be configured to identify the scan line pattern 125 that contains the minimum amount of bowel gas within an internal cavity of the subject. In additional examples, the data processor 122 may be configured to apply one or more thresholding algorithms to identify when a feature 121, or sub-feature thereof, exceeds an intensity or resolution threshold, thereby identifying the target characteristic 123 of the object 114.

Depending on the one or more features 121 associated with an object 114 to be imaged and/or the target characteristic(s) 123 assessed by the data processor 122, the specific type of data utilized by the data processor may also vary. For example, identifying and measuring different physical parameters of a hypo- or hyperechoic feature 121, e.g., cross-sectional width, length, etc., may be performed by analyzing grayscale image data gathered by the data acquisition unit 110. By contrast, twinkling artifact analysis may be performed by processing color flow (Doppler) signals identified in scan-converted data. To determine an amount of a gaseous substance, e.g., bowel gas, present at a specific location along a 2D image plane, harmonic signals may be processed by the data processor 122, prior to grayscale image processing. A signal processor, such as signal processor 118, may be configured to derive such diverse types of ultrasound data and convey this data to the data processor 122. The data processor 122 may be configured to analyze a variety of features due to its ability to analyze B-mode, Doppler, and/or color-mode data in one or more embodiments.

After identifying the image data set 119 that includes the target characteristic 123, the data processor 122 may be configured to select the scan line pattern 125 that corresponds to the identified image data set. Based on the determination made by the data processor 122, the scan line controller 120 may be configured to automatically steer the ultrasound sensor array 112 to emit ultrasound beams 111 in accordance with the target scan line pattern 125 to generate an ultrasound image of the object 114. In this manner, the object 114 is imaged in the target scan line pattern 125 without user manipulation of the ultrasound probe or user interpretation of any image planes displayed on a user interface.

The image of the object 114 obtained along the target scan line pattern 125 may satisfy one or more thresholds indicative of image quality. For instance, the resolution of the object may satisfy a threshold level. In some examples, the amount of the object appearing in the image may exceed a threshold. In another example, the intensity of the object appearing in the image may exceed a threshold.

The user interface 124 may include a display screen configured to display ultrasound images obtained via the ultrasound data acquisition unit 110 and processed via the data processor 122. In some examples, the display screen may be configured to selectively display only certain images obtained via one or more scan line patterns, thereby preventing the display of other images obtained while scanning the 3D volume. For instance, in some embodiments the display screen may be configured to only display the image of the object obtained responsive to the target scan line pattern 125 without displaying images from the other scan line patterns. The user interface 124 may also include a screen for displaying ultrasound images during and/or after the scan. For example, after the target scan line pattern 125 has been identified, the scan line controller 120 may automatically control the sensor array 112 to obtain additional images (e.g., in real-time) only in accordance with the target scan line pattern 125 (e.g., without scanning other portions of the volume until movement is detected) and the additional images may be displayed in real-time on a display. In some embodiments, the user interface 124 may be configured to display ultrasound images only after the target scan line pattern 125 has been identified, such that only images of the selected feature obtained using the targeted scan line pattern are viewable. In other embodiments, the user interface 124 may be configured to display an indication, e.g., a graphic or icon, on the display screen when the screen is displaying an image obtained via the target scan line pattern 125.

The scan line controller 120 may also be configured to control the ultrasound sensor array 112 to automatically re-scan the 3D volume and re-acquire image data therefrom upon detection of movement of the sensor array 112. Image data re-acquisition may be necessary if, for example, the user or the patient inadvertently or intentionally moves the ultrasound sensor array 112 from a first position to a second position. Due to the different position and/or angular orientation of the sensor array 112 in the second position, the previously identified target scan line pattern 125 may no longer acquire image data that contains the target characteristic 123, thus necessitating a fresh scan of the 3D volume to re-identify the target scan line pattern 125 and image the object 114.

After identifying the target scan line pattern 125 for imaging the feature, the system 100 may be further configured to perform additional, automated processing steps. For instance, if a lung is being imaged, the system 100 may be configured to detect lung sliding, B-lines for extravascular lung water evaluation, and/or tissue/fluid consolidation indicative of pneumonia. Various conditions may be programmed into the system 100 and associated with each feature to be imaged. Some embodiments may include options for a user to control whether additional interrogation of the imaged feature is to be pursued. Such options may be selected before and/or after the target scan line pattern 125 has been identified.

In additional embodiments, the system 100 may be configured to conduct continuous, or at least repetitive, processing over a certain length of time. Specifically, the system 100 may be configured to periodically identify the target scan line pattern 125, implementing scan line pattern adjustments as necessary such that optimal images of the object 114 are obtained over time without the need for manual intervention. Particular circumstances may necessitate this type of continuous processing. For example, a patient in an ICU may require repeated monitoring of the lungs. In such cases, the ultrasound sensor array 112 may be coupled to the patient's chest, using an adhesive or other means, and the procedure for identifying the target scan line pattern 125 repeated at specified intervals.

The system 100 may be used to diagnose and/or evaluate a number of conditions, including pneumothorax, pneumonia, and heart failure, for example.

Figure 2:
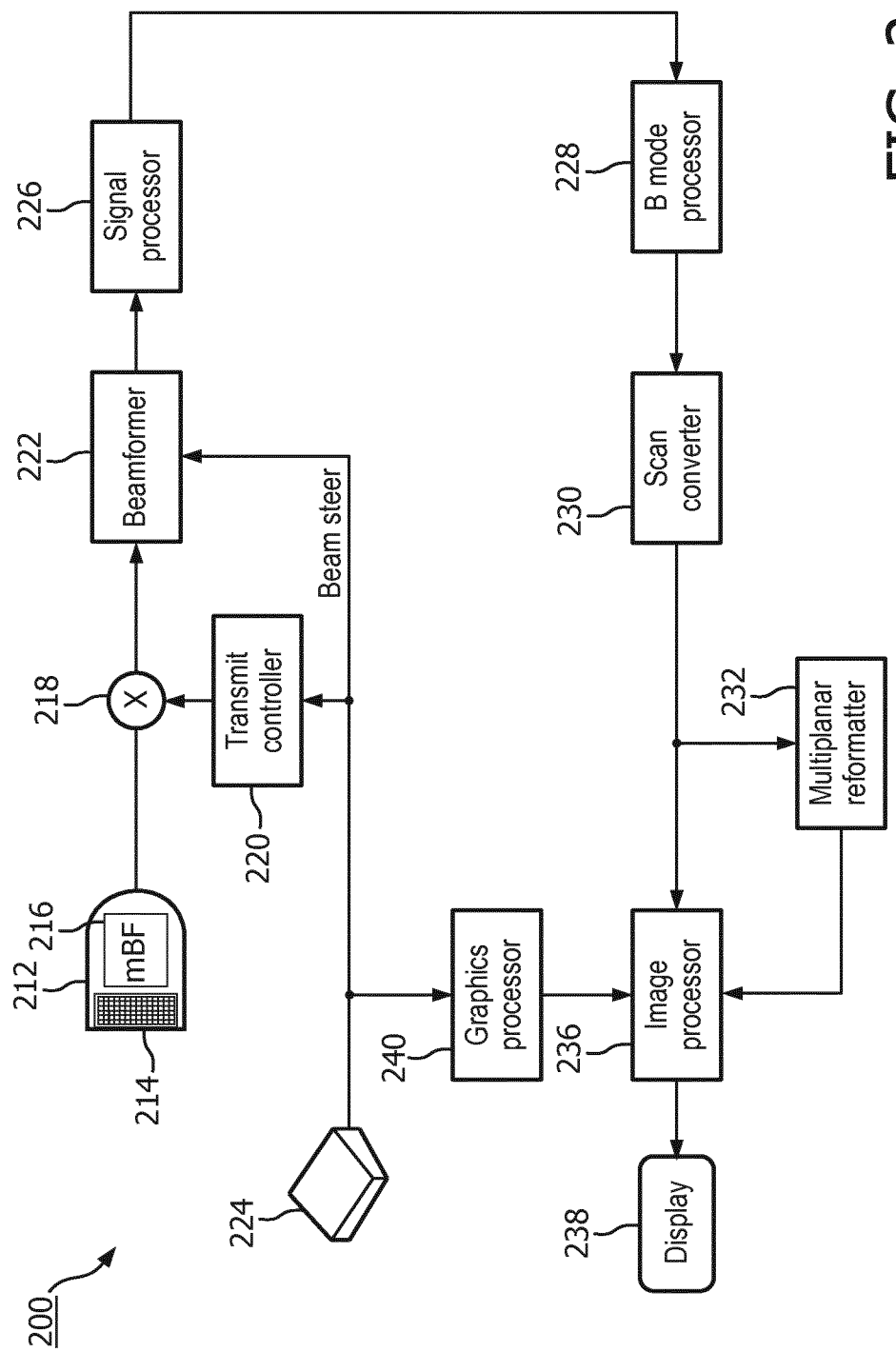
FIG. 2 is a block diagram of another ultrasound imaging system in accordance with the principles of the present disclosure.

FIG. 2 illustrates an ultrasound imaging system 200 constructed in accordance with the principles of the present invention. One or more components shown in FIG. 2 may be included within a system configured to identify a target scan line pattern for imaging one or more selected features. For example, any of the above-described functions of the scan line controller 120 and the data processor 122 may be programmed, e.g., via computer executable instructions, into an existing processor of the system 200. In some examples, the functions of the data processor 122 may be implemented and/or controlled by one or more of the processing components shown in FIG. 2, including for example, the B mode processor 228, scan converter 230, multiplanar reformatter 232, and/or image processor 236.

In the ultrasonic imaging system of FIG. 2, an ultrasound probe 212 includes a transducer array 214 for transmitting ultrasonic waves along a plurality of scan line patterns and receiving echo information. The transducer array 214 may be a matrix array that includes a plurality of transducer elements configured to be individually activated. In other embodiments, the transducer array 214 may be a one-dimensional linear array. The transducer array 214 is coupled to a microbeamformer 216 in the probe 212 which may control the transmission and reception of signals by the transducer elements in the array. In the example shown, the microbeamformer 216 is coupled by the probe cable to a transmit/receive (T/R) switch 218, which switches between transmission and reception and protects the main beamformer 222 from high energy transmit signals. In some embodiments, the T/R switch 218 and other elements in the system can be included in the transducer probe rather than in a separate ultrasound system base. The transmission of ultrasonic beams from the transducer array 214 under control of the microbeamformer 216 is directed by the transmit controller 220 coupled to the T/R switch 218 and the beamformer 222, which receives input, e.g., an indication of a feature to be imaged, from the user's operation of the user interface or control panel 224. One of the functions controlled by the transmit controller 220 is the direction in which beams are steered. Beams may be steered straight ahead from (orthogonal to) the transducer array, or at different angles for a wider field of view. The partially beamformed signals produced by the microbeamformer 216 are coupled to a main beamformer 222 where partially beamformed signals from individual patches of transducer elements are combined into a fully beamformed signal.

The beamformed signals are coupled to a signal processor 226. Like signal processor 118, signal processor 226 may process the received echo signals in various ways, such as bandpass filtering, decimation, I and Q component separation, and harmonic signal separation. Data generated by the different processing techniques employed by the signal processor 226 may be used by a data processor to identify different objects, features, target characteristics, and/or parameters thereof. The signal processor 226 may also perform additional signal enhancement such as speckle reduction, signal compounding, and noise elimination. The processed signals may be coupled to a B mode processor 228, which can employ amplitude detection for the imaging of structures in the body, including the heart, the pleural interface of the lungs, and/or one or more blood vessels, for example. The signals produced by the B mode processor are coupled to a scan converter 230 and a multiplanar reformatter 232. The scan converter 230 arranges the echo signals in the spatial relationship from which they were received in a desired image format. For instance, the scan converter 230 may arrange the echo signals into a two dimensional (2D) sector-shaped format. The multiplanar reformatter 232 can convert echoes which are received from points in a common plane in a volumetric region of the body into an ultrasonic image of that plane, as described in U.S. Pat. No. 6,443,896 (Detmer). The images are coupled from the scan converter 230 and multiplanar reformatter 432 to an image processor 236 for further enhancement, buffering and temporary storage for display on an image display 238. The graphics processor 240 can generate graphic overlays for display with the ultrasound images. These graphic overlays can contain, e.g., standard identifying information such as patient name, date and time of the image, imaging parameters, and the like. Graphic overlays may also include one or more signals indicating the target scan line pattern has been obtained and/or the system 200 is in the process of identifying the target scan line pattern. The graphics processor may receive input from the user interface 224, such as a typed patient name. The user interface 224 may also receive input prompting adjustments in the settings and/or parameters used by the system 200. The user interface can also be coupled to the multiplanar reformatter 232 for selection and control of a display of multiple multiplanar reformatted (MPR) images.

Figure 3:
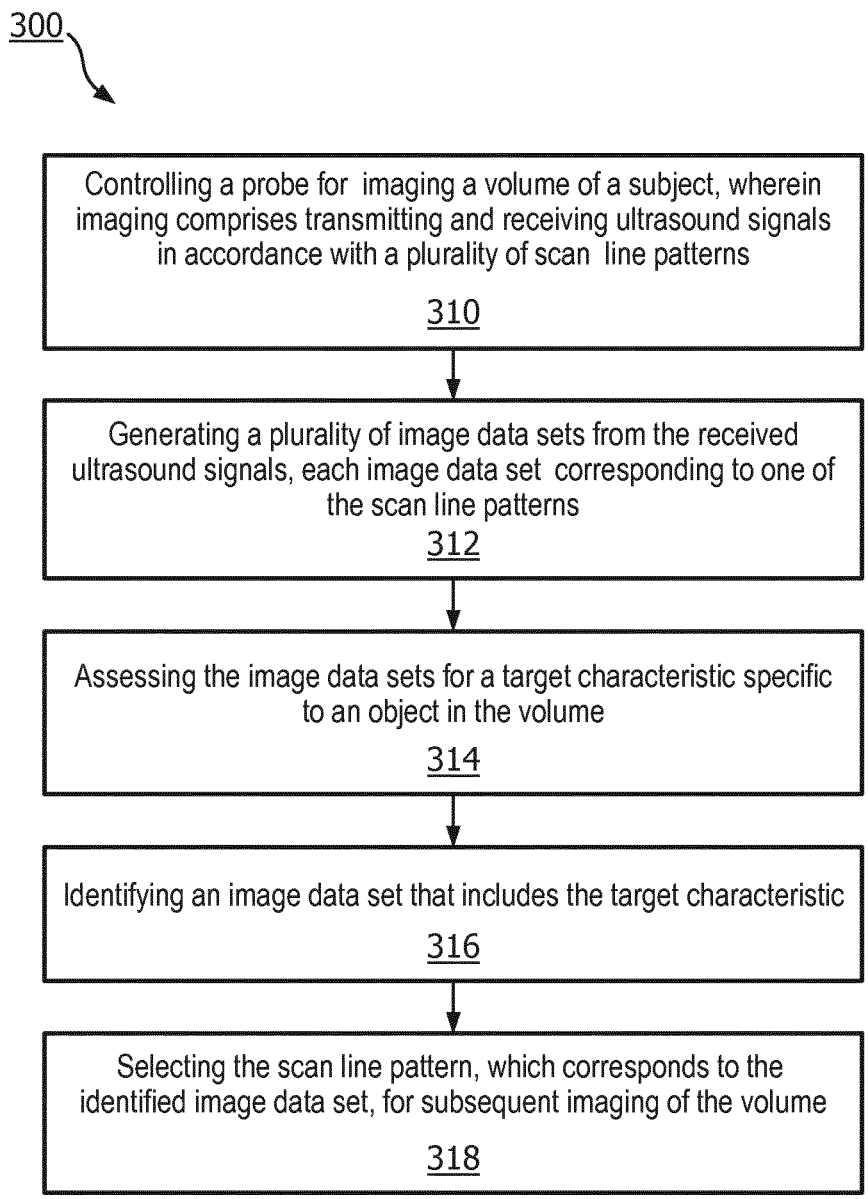
FIG. 3 is a block diagram of an ultrasound imaging method in accordance with the principles of the present disclosure.

FIG. 3 is a block diagram of an ultrasound imaging method in accordance with the principles of the present disclosure. The example method 300 of FIG. 3 shows the steps that may be utilized, in any sequence, by the systems and/or apparatuses described herein for optimizing or improving the scan line pattern used to image a particular bodily object or feature thereof. The method 300 may be performed by an ultrasound imaging system, such as system 100, or other systems including, for example, a mobile system such as LUMIFY® by Koninklijke Philips N.V. ("Philips"). Additional example ultrasound imaging systems may include SPARQ® and/or EPIQ®, also produced by Philips.

In the embodiment shown, the method 300 begins at block 310 by "controlling a probe for imaging a volume of a subject, wherein imaging comprises transmitting and receiving ultrasound signals in accordance with a plurality of scan line patterns." A scan line controller, for example, may execute the actions recited at block 310. In embodiments, the probe may be a matrix, linear, curved-linear, or sector probe. In some examples, the method 300 may further involve, before controlling the probe, receiving an indication of an object to be imaged. Such an indication may be received responsive to a user input, at a user interface, for example. The object may include various organs, sub-portions of organs, or various other structures. In a particular embodiment, the object may be a lung.

At block 312, the method 300 involves "generating a plurality of image data sets from the received ultrasound signals, each image data set corresponding to one of the scan line patterns." One or more processors may be involved in generating the plurality of image data sets. The processors may comprise a sub-component of the ultrasound probe, or a separate component communicatively coupled thereto. Because ultrasound beams may be successively stepped (or rotated, for example) through a 3D volume, the conversion of ultrasound echoes responsive to these beams may yield a plurality of discrete image data sets. Each data set may correspond to a single scan line pattern, such that analyzing each data set may yield information about the quality or contents of each scan line pattern with respect to the targeted object.

At block 314, the method 300 involves "assessing the image data sets for a target characteristic specific to an object in the volume." Various processors may be utilized for assessing the image data sets. Data sets may be assessed by comparing multiple data sets, which may occur on a frame-by-frame basis or at the end of a full scan. Particular embodiments, may also involve weighting certain characteristics within each data set against each other to identify the target characteristic.

At block 316, the method 300 involves "identifying an image data set that includes the target characteristic." The target characteristic may vary depending on the object. In some examples, the target characteristic may be selected automatically by a system implementing the method 300, prior to scanning. In other embodiments, the target characteristic may be selected after scanning is performed, based on the data received at the ultrasound probe. For example, if two or more target characteristics are associated with an object to be imaged, the data may reveal that only one of those target characteristics is discernable from the scan line patterns employed. In this example, that target characteristic may be selected by default. In additional examples, certain target characteristics may be assigned greater priority than others, such that even weak echo signals representative of a certain, high-priority target characteristic may suffice to select that characteristic for further processing. The target characteristic may be a characteristic of the object that meets an image quality threshold and/or an intensity level of a feature specific to the object. The target characteristic may also include the mere presence of a feature, e.g., a plurality of A-lines or a pleural line, specific to the object, e.g., a lung. In some examples, identifying the target characteristic may involve identifying one or more hypo- and/or hyperechoic features in at least one of the image data sets.

The method 300 at block 318 involves "selecting the scan line pattern, which corresponds to the identified image data set, for subsequent imaging of the volume." The selected scan line pattern that includes the target characteristic may provide an optimal image of the object relative to the other scan line patterns. Block 318 may also be performed by one or more processors, which may communicate the selected scan line pattern to the controller used to manipulate the probe and the sensor array included in the probe. Accordingly, after selecting the scan line pattern, embodiments may involve obtaining real-time images of the object in accordance with the selected scan line pattern. These images may be displayed on a display screen.

In some examples, the method may extend beyond block 318. For instance, the method may further involve adjusting one or more parameters used to scan a 3D volume or process the data gleaned from such scanning. For instance, the method 300 may involve selecting a scan speed. The scan speed may refer to the speed at which the ultrasound beams are swept, either mechanically or electronically, through the 3D volume. Other parameters that may be adjusted in accordance with the selected scan line pattern include transmit focal depth, transmit pulse characteristics, scan line spacing, receive filtering bands, spatial compounding, etc., all ultrasound acquisition and processing well known in the art.

Figure 4:
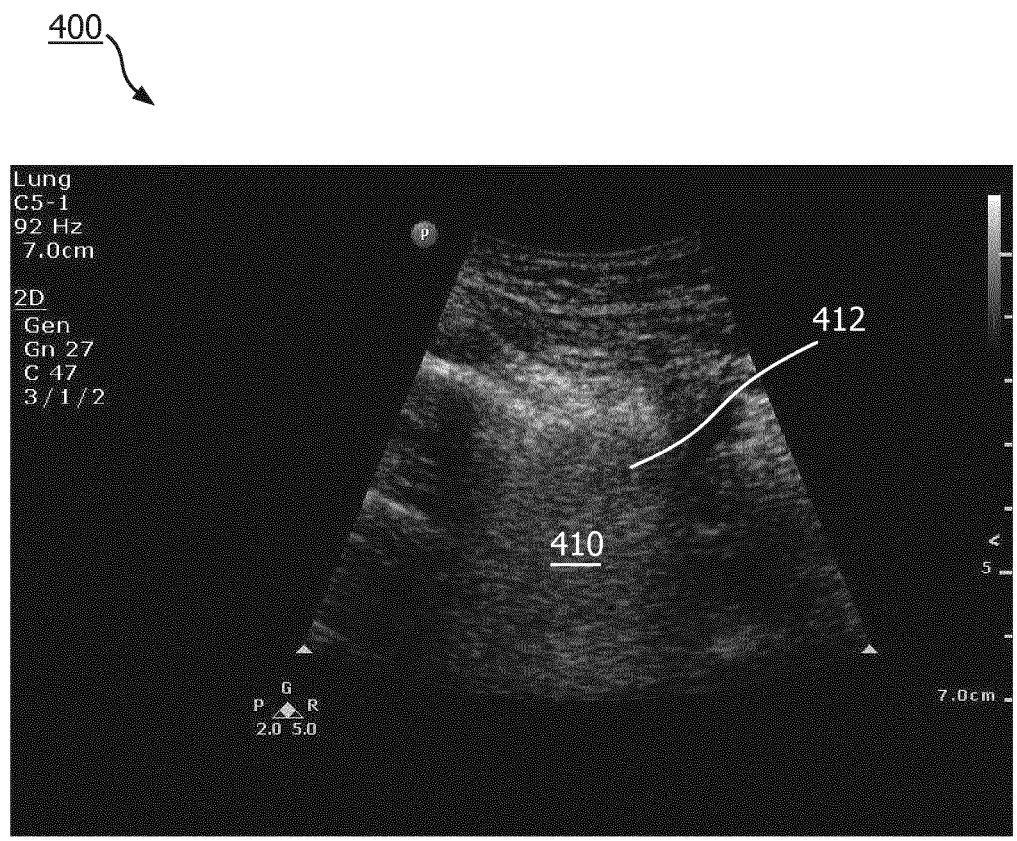
FIG. 4 is a lung ultrasound image obtained via a sub-optimal scan line pattern in accordance with the principles of the present disclosure.

FIG. 4 shows a lung ultrasound image 400 obtained from a sub-optimal scan line pattern. FIG. 4 shows a lung 410 and a pleural line 412 displayed in a B-mode image. As shown, the pleural line 412 is unclear, with the interface between lung tissue and air appearing ill-defined and fuzzy. Due to this lack of image clarity, examination of the pleural line and/or the lung may be difficult, which may interfere with or even render inoperable one or more assistance features that may be reliant on pleural line detection, for example. A clinician examining FIG. 4 may be unable to identify certain lung characteristics including, for example, the thickness of the pleural interface and/or the occurrence of lung sliding.

Figure 5:
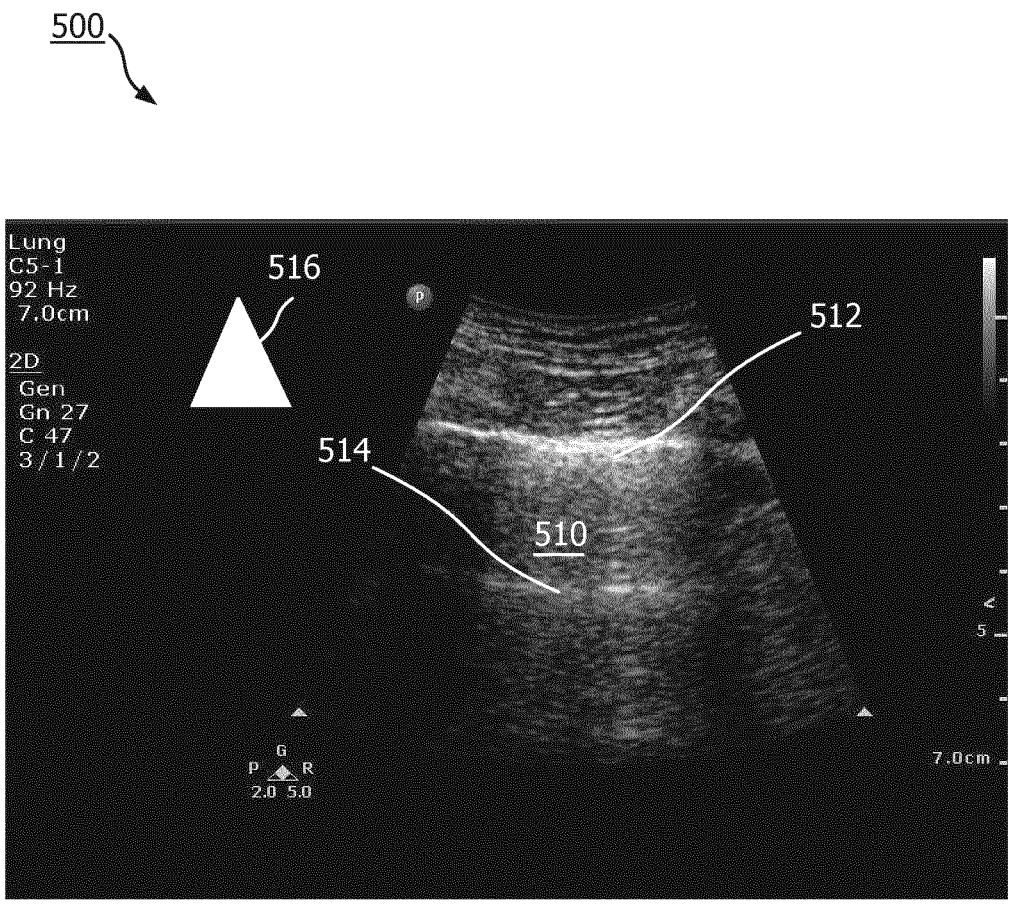
FIG. 5 is a lung ultrasound image taken along a selected scan line pattern in accordance with the principles of the present disclosure.

FIG. 5 shows a lung ultrasound image 500 obtained in a scan line pattern according to the embodiments described herein. FIG. 5 depicts a lung 510 that includes a pleural line 512 and an A-line 514. FIG. 5 also depicts an example of an indicator 516 displayed on the screen when the image of the object taken along the selected scan line pattern is being displayed. Relative to FIG. 4, the pleural line 512 is noticeably brighter, clearer, and otherwise more visible in the selected scan line pattern. The A-line 514 appears at approximately twice the depth of the pleural line 512. The indicator 516 displayed in FIG. 5 may indicate to a user that the lung and/or pleural line 512 shown in the image 500 represents the image produced by a selected scan line pattern. In the embodiment shown, the indicator 516 is a green, triangular graphic. In other embodiments, the indicator 516 may be any other shape, color, and/or size. The position of the indicator 516 on the user interface may also vary. As shown, the indicator 516 is positioned in an upper left corner, however, in other examples, the indicator 516 may be positioned elsewhere. In some embodiments, the indicator 516 might not include a displayed graphic at all, instead including an audio cue and/or tactile stimulation, for example. Using the image 500 shown in FIG. 5, a clinician may be able to identify various characteristics of the lung, as well as other features in the chest region of the subject. Automated identification processes that rely on pleural line and/or lung feature detection may also be performed with greater ease and accuracy using the image 500.

Figure 6A:
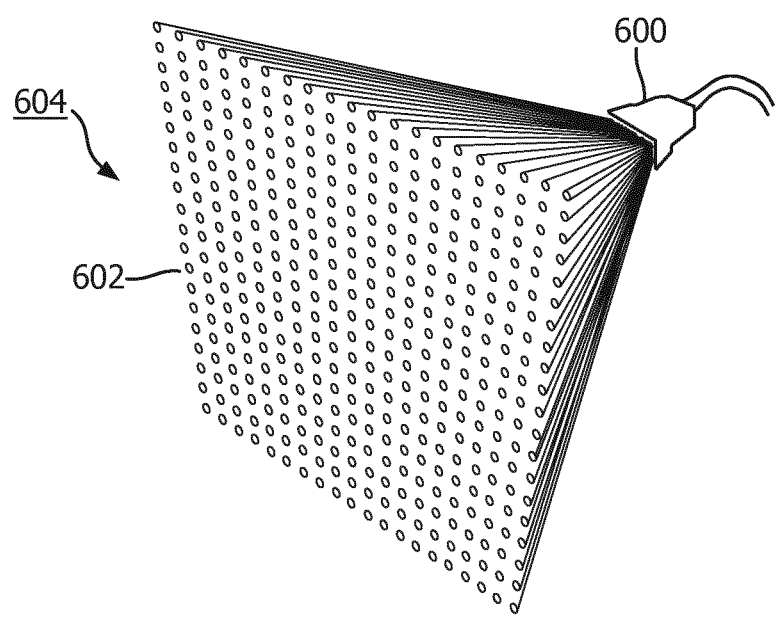
FIG. 6A is an illustration of an example of a scan line pattern which may be transmitted from an ultrasound probe in accordance with the principles of the present disclosure.
Figure 6B:
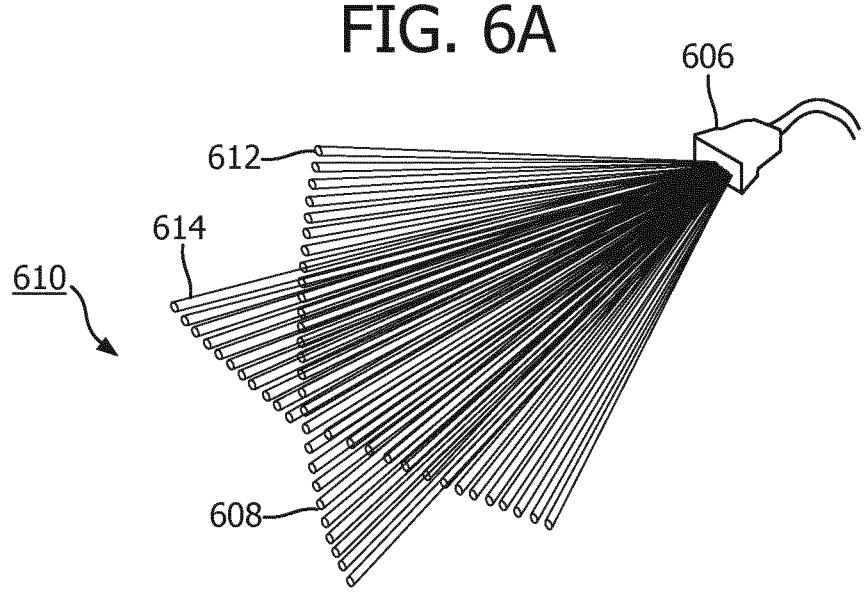
FIG. 6B is an illustration of another example of a scan line pattern which may be transmitted from an ultrasound probe in accordance with the principles of the present disclosure.

Systems and methods according to the present disclosure may involve transmitting ultrasound and receiving ultrasound echoes along any of a variety of scan line patterns, two examples of which are illustrated in FIGS. 6A and 6B. In the example in FIG. 6A an ultrasound probe 600 is configured to transmit (via a sensor array) and responsive to control, e.g., from a scan line controller 120 (not shown), ultrasound signals and receive echoes along a plurality of scan lines 602 which collectively form the scan line pattern 604 and which can be used to image a volumetric region within the subject. The scan line pattern 604 shown in FIG. 6A may be referred to as a "complete interrogation pattern" because ultrasound signals are being transmitted along all scan lines within the field of view of the sensor array. The scan line pattern 604 may be used to scan a volume for an object of interest, or feature thereof, in accordance with the disclosures herein. It will be understood that in other examples, a scan line pattern according to the present disclosure may not transmit and/or receive along all lines but may instead energize one or more select apertures (e.g., a subset of the elements) of the array to ultrasonically scan the region of interest.

FIG. 6B is an illustration of another example scan line pattern, which may be used in accordance with the principles of the present disclosure. In FIG. 6B, an ultrasound probe 606 is configured to transmit and receive (via a sensor array, and responsive to a controller) ultrasound energy along a plurality of scan lines 608 in accordance with a second scan line pattern 610. As shown, in the second scan line pattern 610 ultrasound energy is transmitted and/or received only along a subset of the scan lines as compared to those employed in the scan line pattern 604 depicted in FIG. 6A. The second scan line pattern 610 can be used to obtain imaging data for two orthogonal scan planes 612 and 614, each image plane reconstructed from signals received along the plurality of scan lines in the respective plane. Other scan line patterns may be used in other embodiments, for example radial scan line patterns in which ultrasound energy is transmitted along lines generally within the center of the array and radiating outward or a scan line pattern in which the scan lines are generally parallel to one another.

The 3D scan line patterns 604, 610 depicted in FIGS. 6A and 6B and described represent only a few examples among many possible variations. For example, a given scan line pattern may include one or more discrete scan planes, such as planes 612 and 614. The scan planes may intersect, overlap, or remain separate, e.g., parallel. However, a scan plane merely constitutes an example scan line pattern. Accordingly, scan line patterns in other embodiments may include zero scan planes, instead featuring a pattern of scan lines arranged in a different manner. In some embodiments, scan line patterns may be arcuate, punctate or may comprise various shapes, e.g., frustums, slabs or wedges. The scan line patterns may include scan lines that converge but do not cross. The systems disclosed herein may be configured to alternate between various scan line patterns by adjusting element delays, thus interrogating an entire volume for a target characteristic of an object of interest.

Of course, it is to be appreciated that any one of the examples, embodiments or processes described herein may be combined with one or more other examples, embodiments and/or processes or be separated and/or performed amongst separate devices or device portions in accordance with the present systems, devices and methods. The above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
a user interface configured to receive an indication of an object to be imaged from a user;
a controller configured to control a probe for imaging a volume of a subject based on the indication of the object to be imaged, wherein the imaging comprises transmitting and receiving ultrasound signals in accordance with a plurality of scan line patterns; and
one or more processors in communication with the probe, the one or more processors configured to:
generate a plurality of image data sets from the received ultrasound signals, each image data set of the plurality of image data sets corresponding to one of the plurality of scan line patterns;
select a target characteristic specific to the object to be imaged from a group of characteristics comprising at least one tangible anatomical feature and at least one visual artifact of ultrasound imaging;
derive one or more types of data from the plurality of image data sets based on the target characteristic selected;
assess the plurality of image data sets for the target characteristic specific to the object to be imaged utilizing the one or more types of data specific to the target characteristic;
identify an image data set of the plurality of image data sets that includes the target characteristic; and
select a scan line pattern of the plurality of scan line patterns which corresponds to the image data set of the plurality of image data sets for subsequent imaging of the volume in accordance with the selected scan line pattern of the plurality of scan line patterns.

2. The ultrasound imaging system of claim 1, wherein the target characteristic is a characteristic of the object that meets an image quality threshold.

3. The ultrasound imaging system of claim 2, wherein the target characteristic is an intensity level of a feature specific to the object.

4. The ultrasound imaging system of claim 3, wherein the object is a lung and the feature is a pleural line.

5. The ultrasound imaging system of claim 1, wherein the target characteristic is a presence of a feature specific to the object.

6. The ultrasound imaging system of claim 5, wherein the object is a lung and the feature is a plurality of A-lines at multiple distances of a depth of a pleural line.

7. The ultrasound imaging system of claim 1, wherein the plurality of scan line patterns correspond to a plurality of image planes.

8. The ultrasound imaging system of claim 1, wherein the target characteristic comprises a length or an area of a feature specific to the object.

9. The ultrasound imaging system of claim 1, wherein the controller is further configured to control the probe for the imaging the volume of the subject by re-transmitting and receiving ultrasound signals in accordance with the plurality of scan line patterns upon detection of movement of the probe.

10. The ultrasound imaging system of claim 1, further comprising the probe, wherein the probe is a matrix probe and wherein the transmitting comprises electronically steering the ultrasound signals.

11. The ultrasound imaging system of claim 1, further comprising the probe, wherein the probe is a 1D array probe and wherein the transmitting comprises mechanically sweeping the ultrasound signals.

12. The ultrasound imaging system of claim 1, further comprising a display screen configured to display an image of the object obtained via the selected scan line pattern of the plurality of scan line patterns, which corresponds to the identified image data set, without displaying images obtained via other ones of the plurality of scan line patterns.

13. The ultrasound imaging system of claim 1, wherein the controller is configured to automatically control the probe to obtain a plurality of real-time images in accordance with the selected scan line pattern of the plurality of scan line patterns, the system further comprising a display screen configured to display the plurality of real-time images.

14. The ultrasound imaging system of claim 1, wherein the object comprises a kidney, a heart, a blood vessel, or an internal cavity.

15. The ultrasound imaging system of claim 1, wherein each scan line pattern of the plurality scan line patterns comprises a different shape than remaining ones of the plurality of scan line patterns.

16. The ultrasound imaging system of claim 1, wherein each scan line pattern of the plurality of scan line patterns comprises a different number of image planes than remaining ones of the plurality of scan line patterns.

17. A method comprising:
receiving, from a user at a user interface, an indication of an object to be imaged;
after the receiving the indication, controlling a probe for imaging a volume of a subject based on the indication, wherein the imaging comprises transmitting and receiving ultrasound signals in accordance with a plurality of scan line patterns;
generating a plurality of image data sets from the received ultrasound signals, each image data set of the plurality of image data sets corresponding to one of the plurality of scan line patterns;
selecting a target characteristic specific to the object to be imaged from a group of characteristics comprising at least one tangible anatomical feature and at least one visual artifact of ultrasound imaging;
deriving one or more types of data from the plurality of image data sets based on the target characteristic selected;
assessing the plurality of image data sets for the target characteristic specific to the object to be imaged utilizing the one or more types of data specific to the target characteristic;
identifying an image data set of the plurality of image data sets that includes the target characteristic; and
selecting a scan line pattern of the plurality of scan line patterns which corresponds to the identified image data set of the plurality of image data sets for subsequent imaging of the volume in accordance with the selected scan line pattern of the plurality of scan line patterns.

18. The method of claim 17, wherein the target characteristic is a characteristic of the object that meets an image quality threshold.

19. The method of claim 18, wherein the target characteristic is an intensity level of a feature specific to the object.

20. The method of claim 17, wherein the target characteristic is a presence of a feature specific to the object.

21. The method of claim 20, wherein the object is a lung and the feature is a plurality of A-lines at multiple distances of a depth of a pleural line.

22. A non-transitory computer readable medium comprising instructions, which when executed by one or more processors cause an ultrasound imaging system to perform the method according to claim 15.

* * * * *